United States Patent [19]
Ma

[11] Patent Number: 5,833,366
[45] Date of Patent: Nov. 10, 1998

[54] METHOD AND APPARATUS FOR DETERMINING METAL FREEZING POINTS

[75] Inventor: Che Keung Ma, Greely, Canada

[73] Assignee: National Research Council of Canada, Ottawa, Canada

[21] Appl. No.: 731,639

[22] Filed: Oct. 16, 1996

Related U.S. Application Data

[60] Provisional application No. 60/0058,310, Oct. 16, 1995.

[51] Int. Cl.⁶ .................................................. G01N 25/04
[52] U.S. Cl. ................................................ 374/26; 374/25
[58] Field of Search ........................................ 374/26, 25

[56] References Cited

U.S. PATENT DOCUMENTS

| | | | |
|---|---|---|---|
| 3,250,115 | 5/1966 | Donnell | 374/25 |
| 3,600,933 | 8/1971 | Johnston | 374/23 |
| 3,667,280 | 6/1972 | Simpson | 374/25 |
| 3,824,837 | 7/1974 | Nagaoka et al. | 374/26 |
| 3,891,834 | 6/1975 | Warisinski | 374/26 |
| 4,383,770 | 5/1983 | Boschung et al. | 374/25 |
| 4,601,587 | 7/1986 | Mathiprakasin | 374/25 |
| 5,141,329 | 8/1992 | Orlando et al. | 374/25 |

FOREIGN PATENT DOCUMENTS

| | | | |
|---|---|---|---|
| 3200991 | 9/1982 | Germany | 374/26 |
| 62-22053 | 1/1987 | Japan | 374/26 |
| 763755 | 9/1980 | U.S.S.R. | 374/25 |

OTHER PUBLICATIONS

Critical viewpoints on the methods of realizing the metal freezing points of the ITS–90 C.K. MA Rev. Scl. Instrum. 66 (8), Aug. 1995 American Institute of Physics p. 4233.

*Primary Examiner*—Diego F. F. Gutierrez
*Attorney, Agent, or Firm*—Ronald G. Bitner

[57] ABSTRACT

A method and apparatus for determining the freezing points of a metal by inducing solidification in a cooling liquid metal sample in a supercooled state and utilizing specific detected peak values or changes in slope in a temperature/time plot as the sample cools, begins solidification and recalesces. It was found that the maximum temperature reached after the second rise, if two rises occur, the maximum of a single rise, or the temperature at which the rate of temperature drop decreases, if no temperature rise occurs, provides a useful approximation of the liquidus temperature and hence the freezing point of the sample.

4 Claims, 3 Drawing Sheets

METHOD AND APPARATUS FOR DETERMINING METAL FREEZING POINTS

This application claims benefit of USC Provisional Application No. 60/005,310, filed Oct. 16, 1995.

BACKGROUND OF THE INVENTION

1. Field of the Invention

This invention relates to a method and apparatus for determining metal freezing points.

2. Description of the Prior Art

The freezing points of the metals Indium, Tin, Zinc, Aluminum, Silver, Gold and Copper are some of the defining fixed points of the International Temperature Scale of 1990. Determination of these fixed points is essential for the establishment and maintenance of this temperature scale. These points can be utilized for the calibration of temperature measuring instruments such as thermocouples and optical pyrometers.

A simple, and common, method of determining the freezing point of a metal involves progressively cooling a molten sample and allowing solidification to occur spontaneously. As the molten sample is cooled it tends to supercool, that is, its temperature falls below the freezing point before solidification begins. As the sample solidifies, it recalesces, that is, the temperature of the sample rises due to the release of latent heat. After the temperature has reached a maximum, it may remain observably constant for some time, resulting in a plateau in a temperature-time plot. Before recalescence has completed, the sample is in a supercooled state and its temperature is not a proper measure of the freezing point. The plateau temperature, which occurs after complete recalescence, is usually taken to be the freezing point.

If the metal were perfectly pure, the plateau temperature is effectively the freezing point. However, the purest metals available are actually dilute alloys of a solvent (base metal) and solutes (impurities). The overall effect of the solutes is such that the freezing temperature of the alloy is depressed from the freezing point of the solvent. Some solutes depress the freezing temperature of the alloy, while others elevate it. Alloys with solutes with a collective freezing temperature depressing effect are known as the k<1 type while alloys with a collective temperature elevating effect are known as the k>1 type. Since most solutes in a typical alloy are of the temperature-depressing kind (k<l), the overall effect of the solutes is to cause the freezing temperature of the alloy to be depressed from the freezing point of the solvent. In addition, as more solid grows by accretion, preferential segregation of the temperature-depressing solutes into the liquid increases the solute concentration in the liquid and results in progressive decrease in the temperature at the interface where solidification occurs. At the onset of solidification the amount of solidified material is minute and there is effectively no increase of solute concentration in the liquid. If the sample is not in a supercooled state, we find that the temperature at the interface between the solid and liquid portions that is least depressed from the freezing point would occur at the onset of solidification. As a result, the temperature that is closest to the freezing point occurs under the condition in which the amount of solid is minute and is in equilibrium (both thermally and constitutionally) with the liquid. The determination of this equilibrium temperature, the liquidus point of an alloy sample, is the goal in the determination of the freezing point of the pure metal.

In principle, the liquidus point can be obtained by measuring the temperature of a nearly molten sample that is maintained so that a minute amount of solid is in equilibrium with the remaining liquid portion. In practice, however, the equilibrium condition is unobtainable in freezing and undetectable in melting. In freezing, solidification begins in a supercooled liquid and resulting solid is not in thermal equilibrium with the liquid. In melting, the effect of the solid-to-liquid phase change of the minuscule amount of solid at the end of melting is too small to be measurable, and therefore the existence of it is undectable.

As indicated above, the determination of a temperature approximating the freezing point can be more readily obtained by using a relatively pure metal, with the detection of the plateau temperature. However, for an metal which is not sufficiently pure, the effect of increasing concentration in the liquid causes the inerface temperature to decrease during recalescence, producing no detectable temperature plateau, and thus making determination of the freezing point difficult. For many applications it would be desirable to be able to use a less pure and more readily available grade of the metal.

SUMMARY OF THE INVENTION

An object of the present invention is to provide a method for determining metal freezing points.

Another object of the present invention is to provide an apparatus for determining metal freezing points.

Another object of the present invention is to provide a method and apparatus that allows determining metal freezing points with a less pure metal sample.

It has been found that by inducing solidification in a cooling liquid metal sample that is near the liquidus point, the temperature/time profile can be utilized to determine the liquidus point. Depending on whether solidification is induced above, at, or below the liquidus point, a limited number of temperature/time patterns are produced which can be utilized by detecting either changes in slope or the peaks of the temperature/time profile. Specifically, if solidification is induced above or at the liquidus point, a detectable reduction in the cooling rate will be produced at the liquidus point. If solidification is induced below the liquidus point, one or two peaks are produced due to recalescence. It was found that the maximum temperature reached at the second rise, if two rises occur, or the maximum of a single rise, provides a useful approximation of the liquidus temperature and hence the freezing point.

Solidification can be induced at the anticipated freezing point by various methods, examples of which are described herein.

The present invention provides a method of determining the freezing point of a metal sample comprising cooling the metal sample from a liquid state to a temperature anticipated to be near the liquidus temperature of the metal sample; while continuing the cooling of the metal sample, contacting the sample with a metal solid having substantially the same composition and temperature as the sample to induce solidification of the liquid sample as soon as the sample supercools; obtaining a measure of temperature as the sample solidifies; and determining the maximum temperature reached at a second rise, if two temperature rises occur, or the maximum of a single rise, if only one rise occurs, or the temperature at which the rate of temperature drop decreases, if no temperature rise occurs, to provide an approximation of the liquidus temperature and hence the freezing point of the sample.

The present invention also provides an apparatus for determining the freezing point of a metal sample comprising: a sample container for containing a liquid metal sample;

temperature measuring means for providing a measure of the temperature of the sample; cooling means for cooling the sample; and means for contacting the liquid metal sample with a solid metal seed element for inducing solidification of the liquid metal sample.

DESCRIPTION OF THE PREFERRED EMBODIMENTS

Figure 1:
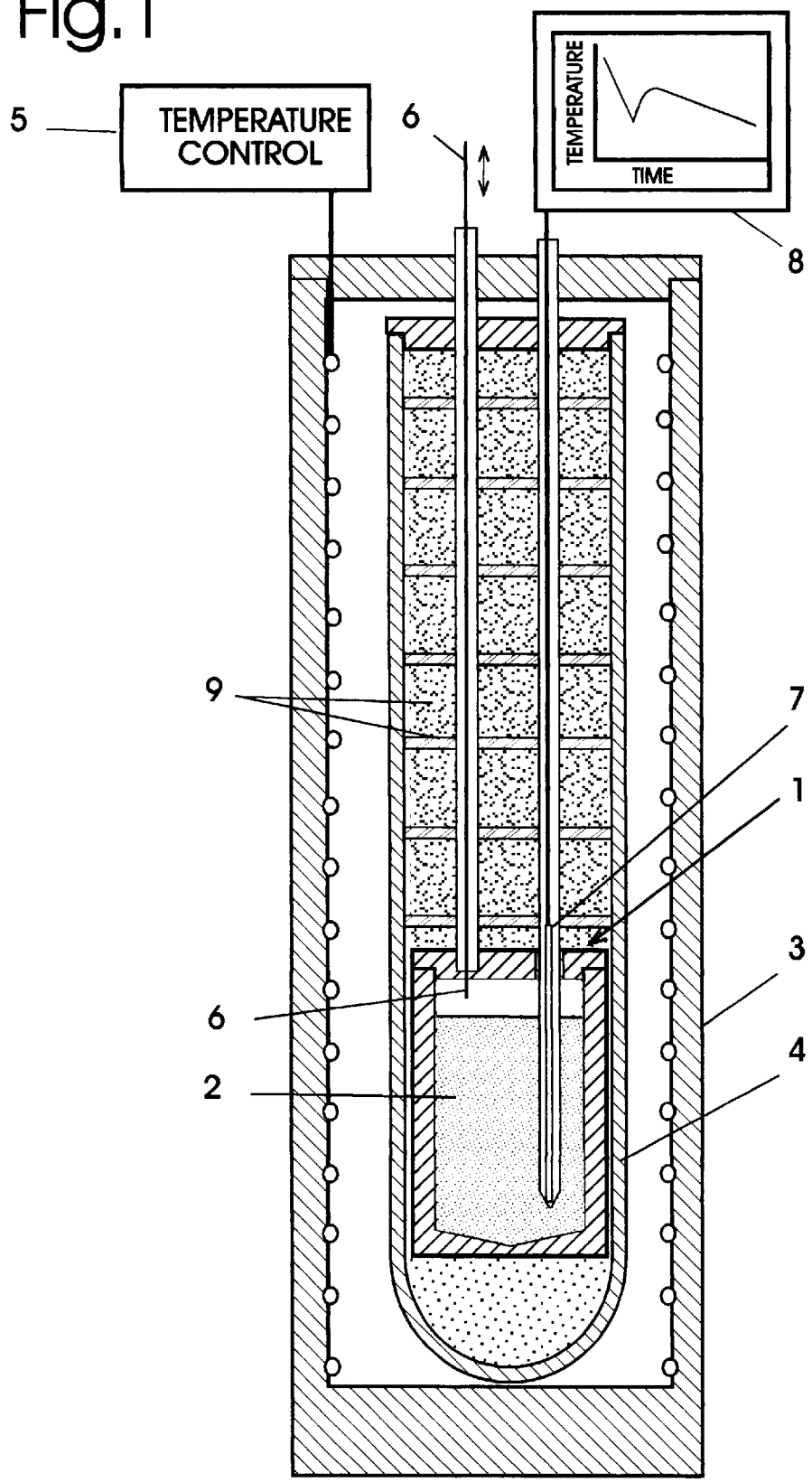
FIG. 1 is a partially schematic and partially sectioned representation of one embodiment of the apparatus of the invention.

With reference to FIG. 1, one embodiment of the apparatus of the present invention comprises a metal sample receiving container 1 disposed within temperature regulating containers 3 and 4 controlled by temperature control means 5, and particularly adapted for the controlled cooling of a liquid sample 2. Suitable insulating components 9 are provided to facilitate temperature regulation.

In accordance with the invention solidification is induced by contact with a solid and specifically by introducing a seed element, shown in the form of a metal wire 6, into the liquid sample 2. The seed element, or wire 6, preferably has a composition and temperature substantially similar to that of the sample when introduced, to avoid disturbing the sample constitutionally and thermally. In particular, to avoid an increase in the solute concentration the seed element should preferably be as pure, or purer, than the sample, ie., having a solute concentration equal to or less than that of the sample.

Temperature measuring means, such as a thermocouple 7, provides a measure of the temperature of the sample 2. Included are suitable recording means 8 for processing the output of the temperature measuring means 7 and recording and/or displaying temperature values as the sample cools.

In operation, the temperature of a liquid sample 2 is controlled by a suitable controller 5 to provide a continuously cooling environment.

Figure 2:
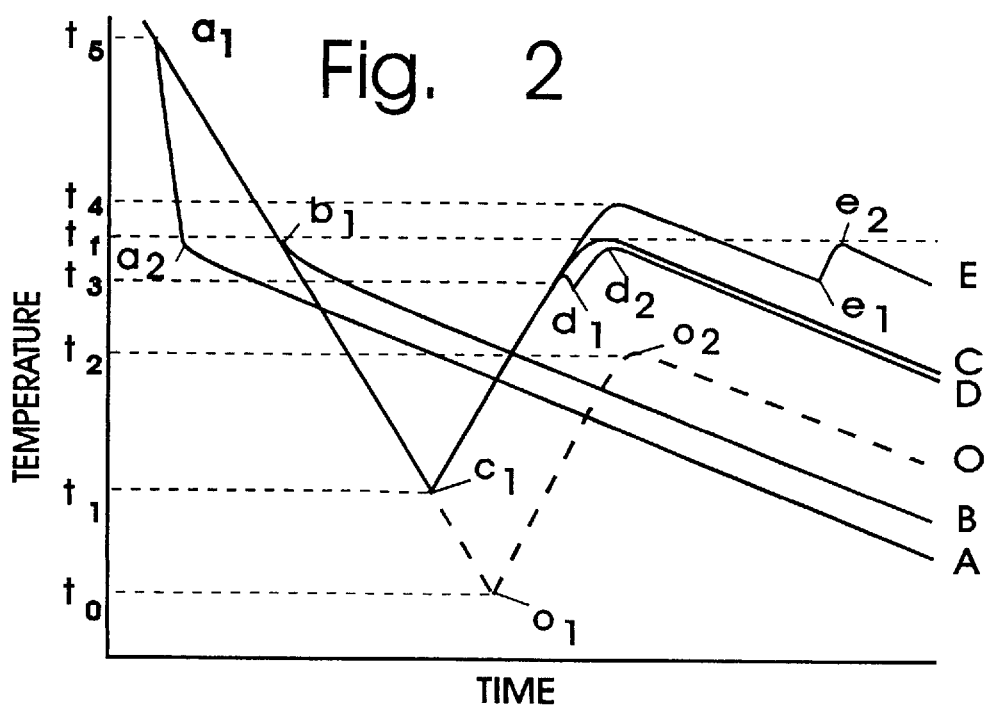
FIG. 2 is a idealized temperature-time plot illustrating various possible results in the freezing of a liquid metal sample with induced solidification.

FIG. 2 is a temperature-time plot showing various possible effects of inducing solidification in the freezing of a liquid metal sample. If the liquid is allowed to cool without intervention, the liquid sample will supercool whereby the temperature will fall well below the liquidus point $t_f$, to a point designated as $O_1$ in FIG. 2, at which point solidification begins. Due to recalescence the temperature of the sample rises to a point $O_2$ at temperature $t_2$ which is below the liquidus temperature $t_f$ and subsequently falls further, as illustrated by curve 0 in FIG. 2.

In accordance with the present invention, with the liquid sample at a temperature anticipated to be about the liquidus temperature, solidification is induced by introducing the wire 6 into the sample. It should be noted, that at this point it may not be known if the temperature of the sample is above, at, or below its liquidus temperature. Also, the variation in the solute concentration of the seed and sample will not be known. As shown in FIG. 2, the seed can be introduced into the liquid at a temperature above ($t_s$ at point $a_1$) at ($t_f$ at point $b_1$), or below ($t_1$ at point $c_1$) the liquidus temperature $t_f$ which results in the curves designated A, B, and C, respectively, in FIG. 2.

Referring to curve A in FIG. 2, if the liquid sample temperature is somewhat above the liquidus temperature, such as at $t_s$, when the seed is introduced into the liquid sample, the melting thereof results in an increased rate of temperature decrease (path $a_1$ to $a_2$. When solidification begins latent heat effects result in a reduction in the rate of temperature drop. The point $a_2$ at which the reduction in the slope occurs approximates the metal freezing point $t_f$. It should be noted that the selected introduction temperature $t_s$ should be sufficiently close to the liquidus temperature so that some amount of the solid metal seed element remains unmelted as the cooler environment lowers the temperature of the sample below the liquidus temperature $t_f$ in order to induce solidification.

If the temperature when the wire is introduced happens to correspond with the liquidus temperature, solidification begins immediately and produces a detectable change in slope at $t_f$ at point $b_2$ as illustrated by curve B.

If the liquid sample temperature is below the liquidus temperature, such as at $t_1$ (point $c_1$, when the seed is introduced, a temperature rise occurs due to recalescence reaching a peak value that corresponds with the liquidus temperature $t_f$ as shown by curve C in FIG. 2.

Figure 3:
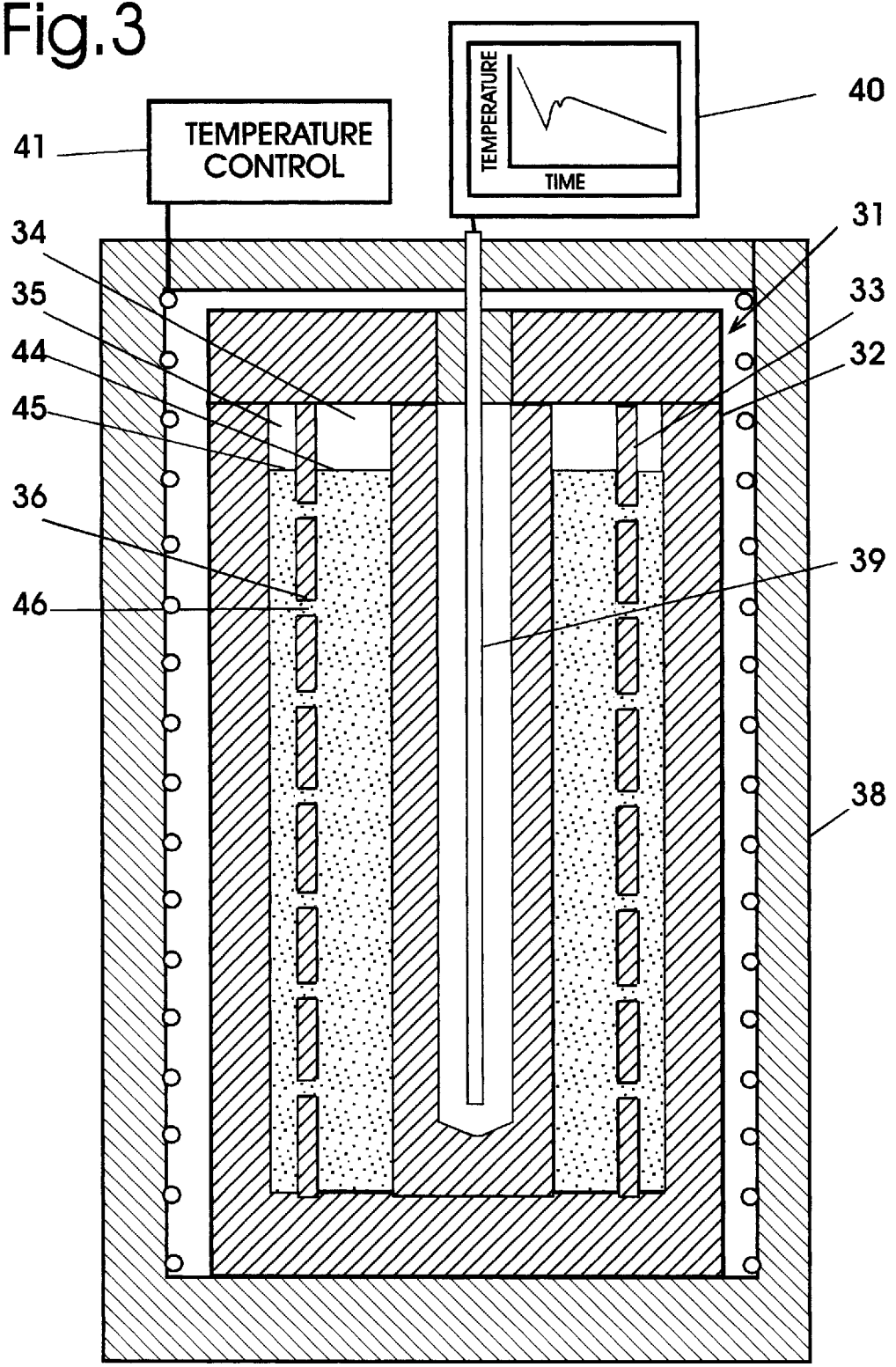
FIG. 3 is a partially schematic and partially sectioned representation of a second embodiment of the apparatus of the invention.

FIG. 3 illustrates a second embodiment of the apparatus of the present invention. The apparatus comprises a sample container 31 having an outer containing wall 32 and an inner partition wall 33 spaced inward from the outer wall. The inner partition wall 33 defines an inner chamber 34 and an outer chamber 35 that surrounds the inner chamber. The partition wall 33 has perforations 36 to allow contact between a sample portion 44 in the inner chamber 34 with a sample portion 45 in the outer chamber 35.

Upon cooling and solidification of the sample portion 45 in the outer chamber 35, the contacting portions 46 of the sample at the perforations 36 of the partition wall 33 define seed elements 46 for the sample portion 44 in the inner chamber 34, as will be described.

The apparatus includes suitable means 41 for controlling the temperature of the sample, and particularly for cooling of a liquid sample to initiate solidification. The sample container is shown disposed in an insulated outer container 38.

Temperature measuring means, such as a thermocouple 39, provides a measure of the temperature of the sample. Included are suitable recording means 40 for processing the output of the temperature measuring means 39 and recording and/or displaying temperature values as the sample cools.

FIG. 2 shows the various possible effects in the freezing of a liquid metal sample, using the apparatus of FIG. 3.

In operation, the temperature is controlled to provide a continuously cooling environment of a sample in the liquid state. With reference to both FIGS. 2 and 3, as the liquid supercools, the sample portion 45 in the outer chamber 35, being outside and therefore cooler, reaches maximum supercooling and begins solidification (at a temperature such as $t_0$), while the sample portion 44 in the inner chamber 34 is at a higher temperature ($t_1$). Due to recalescence in the outer sample portion 45, the temperature of the sample in the inner chamber 34 begins to rise. Eventually the solid part of the sample 45 in the outer chamber 35 grows into the perforations 36 and this induces solidification in the sample portion 44 in the inner chamber 34.

The temperature rise that occurs in the inner sample portion 44, due to recalescence in the outer sample portion 45, may reach a first, or only, peak value that is below ($t_3$), at ($t_f$), or above ($t_4$) the liquidus point $t_f$, as shown in the curves designated D, C, and E, respectively, in FIG. 2.

Consider first that the temperature rises to a peak value ($t_3$,) that is below liquidus point $t_f$. The temperature then decreases as the effect of the cooling environment becomes dominant. When the induced solidification in the inner sample portion takes effect (point $d_1$) the temperature rises again to a temperature that approximates the liquidus temperature $t_f$. Thereafter the curve D resembles a non-induced freezing curve.

In the case where the outer sample portion recalesces to a temperature that is higher than $t_f$, the inner sample portion may be heated to a temperature that is equal to $t_f$ (curve C), or higher than $t_f$ ($t_4$ on curve E). This may happen if the liquidus point of the outer sample portion 45 is higher than $t_f$. Since both the outer sample portion 45 and the inner sample portion 44 are assumed to be the k<1 kind, the liquidus point of the outer sample portion 45 is higher if it is purer. In the case were the outer sample portion is of the k>1 kind, its liquidus temperature is certainly higher than that of the inner sample portion. There is a tendency for the outer sample portion to become the k>1 kind. As the solid-liquid interface advances through the perforations, the k>1 solutes preferentially distribute themselves into the outer sample. As discussed below, the temperature at which induction occurs can be slightly varied by manipulating the cooling rate of the environment. Curve C illustrates the case in which induction occurs as the inner sample portion is heated to a temperature that is equal to $t_f$. In curve E, the inner sample portion is heated to a temperature above $t_f$ to $t_4$, but induction occurs at a temperature lower than $t_f$ at a time indicated by point $e_1$.

In curves D and E in FIG. 2, the maximum temperature after the second temperature rise (points $d_2$ and $e_2$, respectively), is the best approximation to $t_f$. In curve C there is only one temperature rise and the maximum temperature is the best approximation of $t_f$.

In the apparatus of FIG. 3, the perforations 36 of the partition wall 33 must be sufficiently large for viscous liquid metal to flow through. Since the flow is dependent on the height of the liquid, the size of a perforation 36 may decrease as the liquid height above it increase. The partition wall 33 should be thick enough to prevent the dendrites in the outer sample portion from reaching the inner sample portion immediately in order to allow time for the temperature of the inner sample portion to rise. The mass of the outer sample portion 45 should be large enough for the release of sufficient latent heat to raise the temperature of the inner sample portion appropriately. However, the thickness and therefore the mass of the outer sample portion should be small so that, by the time the solid portion in the outer sample portion grows into the perforations, the furnace temperature has not fallen substantially below the liquidus temperature.

In an apparatus as shown in FIG. 3, dimensions that were found to be suitable were as follows: Outside container dimensions 44.5 mm diameter and 110 mm high; outer chamber outside and inside diameters 40.4 mm and 38.1 mm, respectively; inner chamber outside and inside diameters 32.5 mm and 19.1 mm, respectively; a total of 72, 3 mm diameter perforations arranged in 9 circumferentially spaced rows with 8 apertures in each row.

Figure 4:
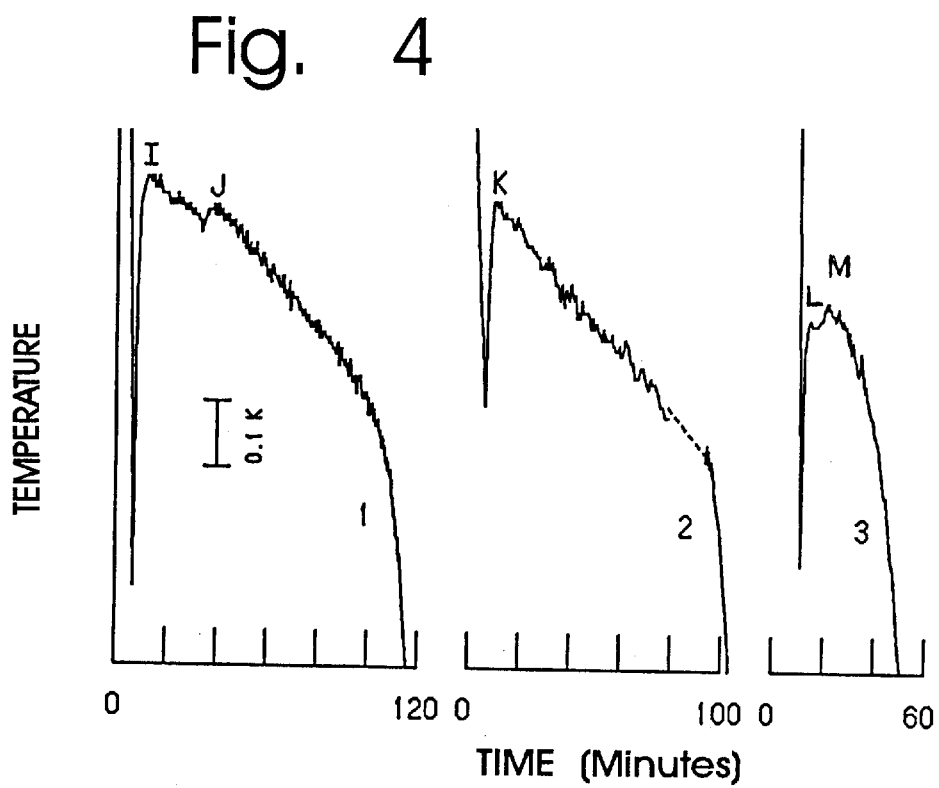
FIG. 4 is a temperature-time plot showing three representative plots obtained with an apparatus as shown in FIG. 3.

FIG. 4 shows three representative plots 1, 2 and 3 obtained for an industrial grade copper sample using an apparatus as illustrated in FIG. 3. The differing plots resulted from differing cooling rates with plot 1 obtained with the slowest cooling rate and plot 3 with the fastest cooling rate. It will be noted that the plots 1, 2 and 3 in FIG. 4 resemble the plots E, C and D, respectively, in FIG. 2. In plot 1 the first rise of the plot is due to the recalescence of the outer sample. However, the maximum temperature (point I) that has been reached may or may not be above the liquidus point $t_f$ of the inner sample. The second rise (point J) is an indication of solidification in the inner sample. In plot 2 the absence of the second rise indicates that solidification (which may or may not be induced at a temperature equal to $t_f$) is occurring at the time indicated by the arrow. In plot 3 the small rise and fall at point L, being steady and lasting a few minutes, are not likely to be measurement fluctuations, and are the true indications of the varying temperature of the inner sample. For all of these three plots the maximum after the second rise (points J and M) or the maximum after the only rise (point K) is the best approximation to the liquidus temperature or freezing point of the sample.

The embodiments of FIG. 1 and 3 illustrate two different means for inducing solidification. It will be appreciated that other means may be utilized. For example, a variation of the embodiment of FIG. 3 may involve the use of a seed element, or elements, in the form of particles, such as shots or pellets that are dropped into the liquid sample.

What is claimed is:

1. A method of determining the freezing point of a metal sample comprising:

cooling the metal sample from a liquid state to a temperature anticipated to be at or near the liquidus temperature of the metal sample;

while continuing the cooling of the metal sample, contacting the sample with a metal solid having approximately the same composition and temperature as the sample to induce solidification of the liquid sample as soon as the sample supercools;

obtaining a measure of temperature to provide a temperature/time profile as the sample solidifies; and from the temperature/time profile determining the maximum temperature reached at a second rise, if two temperature rises occur, or the maximum of a single rise, if only one rise occurs, or the temperature at which the rate of temperature drop decreases, if no temperature rise occurs, to provide an approximation of the liquidus temperature and hence the freezing point of the sample.

2. The method of claim 1, wherein said solid for contacting the sample comprises a wire or particle.

3. The method of claim 1, wherein said solid for contacting the sample comprises a previously solidified portion of the sample.

4. The method of claim 1, wherein said solid for contacting the sample has a solute concentration equal to or less than that of the sample.

* * * * *